(12) United States Patent
Vermeire et al.

(10) Patent No.: US 8,253,422 B2
(45) Date of Patent: Aug. 28, 2012

(54) METHOD OF MANUFACTURE OF WAFERS USING AN ELECTRO-CHEMICAL RESIDUE SENSOR (ECRS)

(75) Inventors: Bert M. Vermeire, Escondido, CA (US); Farhang F. Shadman, Tucson, AZ (US)

(73) Assignee: Environmental Metrology Corporation, Tucson, AZ (US)

( * ) Notice: Subject to any disclaimer, the term of this patent is extended or adjusted under 35 U.S.C. 154(b) by 0 days.

(21) Appl. No.: 13/048,703

(22) Filed: Mar. 15, 2011

(65) Prior Publication Data

US 2011/0180106 A1     Jul. 28, 2011

Related U.S. Application Data

(60) Division of application No. 11/968,726, filed on Jan. 3, 2008, now Pat. No. 7,932,726, which is a continuation-in-part of application No. 11/205,635, filed on Aug. 16, 2005, now Pat. No. 7,317,317, and a continuation-in-part of application No. 11/205,582, filed on Aug. 16, 2005, now Pat. No. 7,332,902, and a continuation-in-part of application No. 11/205,636, filed on Aug. 16, 2005, now Pat. No. 7,489,141.

(51) Int. Cl.
*G01R 31/08*     (2006.01)
(52) U.S. Cl. ...................................................... 324/525
(58) Field of Classification Search .................. 324/525; 134/2, 18
See application file for complete search history.

(56) References Cited

U.S. PATENT DOCUMENTS

| 5,845,660 | A | * | 12/1998 | Shindo et al. | ............... | 134/56 R |
| 5,882,938 | A | * | 3/1999 | Takahashi et al. | ............ | 436/151 |
| 6,241,827 | B1 | * | 6/2001 | Tanaka et al. | ................... | 134/18 |

* cited by examiner

*Primary Examiner* — Amy He
(74) *Attorney, Agent, or Firm* — Eric A. Gifford

(57) ABSTRACT

A method of improving the clean, rinse and dry processes during the manufacture of ICs, MEMS and other micro-devices to conserve solution and energy while completing the process within a specified time. An electro-chemical residue sensor (ECRS) provides in-situ and real-time measurement of residual contamination on a surface or inside void micro features within the sensor representative of conditions on production wafers. The in-situ measurements are used to design and optimize a production process. The wafers are manufactured in accordance with the production process without the ECRS.

8 Claims, 22 Drawing Sheets

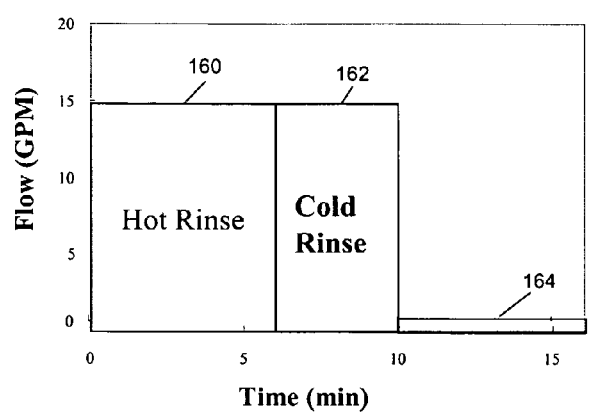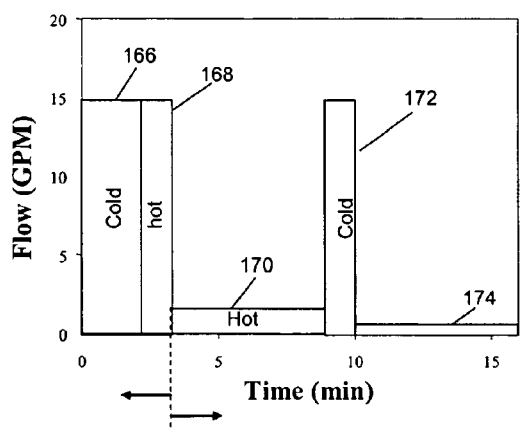
Fig. 8a                    Fig. 8b

METHOD OF MANUFACTURE OF WAFERS USING AN ELECTRO-CHEMICAL RESIDUE SENSOR (ECRS)

CROSS-REFERENCE TO RELATED APPLICATIONS

This applications claims benefit of priority under 35 U.S.C. 120 as a divisional of co-pending U.S. application Ser. No. 11/968,726 entitled "Method Of Design Optimization And Monitoring The Clean/Rinse/Dry Processes Of Patterned Wafers Using An Electro-Chemical Residue Sensor (ECRS)," filed Jan. 3, 2008, which is a continuation-in-part of U.S. application Ser. No. 11/205,635 entitled "Shielded Micro Sensor and Method for Electrochemically Monitoring Residue in Micro Features", now U.S. Pat. No. 7,317,317, Ser. No. 11/205,582 entitled "Micro Sensor for Electro-chemically Monitoring Residue in Micro Channels" now U.S. Pat. No. 7,332,902 and Ser. No. 11/205,636 entitled "Surface Micro Sensor and Method" now U.S. Pat. No. 7,489,141, all filed Aug. 16, 2005, the entire contents of which are incorporated by reference.

BACKGROUND OF THE INVENTION

1. Field of the Invention

This invention relates to monitoring the cleaning, rinsing and drying processes during the manufacture of ICs, MEMS and other micro-devices and more specifically to optimizing the processes to conserve the clean, rinse and dry solutions and energy using an electro-chemical residue sensor (ECRS) for micro-features including surfaces or void micro features.

2. Description of the Related Art

A major challenge in manufacturing of the micro and nano devices is the cleaning and drying of very small void features, particularly those with large aspect ratios. These micro features are fabricated in various processing steps and can be very small voids such as gaps, holes, vias or trenches that are intentionally etched. The micro features can also be pores in a deposited dielectric material. Cleaning and drying occur repeatedly during the processing chain and are responsible for a significant part of the total processing time and for the consumption of much of the water, chemicals and energy.

In semiconductor manufacturing, trenches and vias are fabricated both in the device level and in the interconnect level. Most of these features have high aspect ratios with submicron openings that are oriented perpendicular to the fluid-solid interface of the device to the cleaning fluid and because of their high aspect ratio and very small width are very difficult to clean and dry. In Integrated Circuits, MEMS and other micro device manufacturing, well controlled cleaning and drying are essential to avoid deformation of layers and improper adhesion of moving parts. Improper cleaning and drying would have a significant effect on manufacturing yield and device performance and reliability in both semiconductor and MEMS fabrication. Over-cleaning, over-rinsing or over-drying results in excessive use of chemicals, water and energy and also increases cycle time and potentially causes yield loss. Therefore, there is a strong economic and environmental incentive to use a process that is "just good enough".

The fine structures left behind after processes such as etching, deposition, and patterning, need to be cleaned and the reaction by-products need to be removed often down to trace levels. This usually involves three steps: 1) application of a cleaning solution; 2) rinsing and/or purging using ultra pure water or other rinsing solutions; and 3) drying by removing and purging the traces of any solvents used during rinsing. Due to the undesirable surface tension associated with aqueous chemicals and non-wetting nature of most future dielectrics, industry is pursing the development of processes based on supercritical fluids such as supercritical carbon dioxide for cleaning and pattern development. Measurement of cleanliness under these processing conditions is very critical.

Cleaning, rinsing, and subsequent drying processes are often performed and controlled almost "blindly" and based on trial and error or past experience. The way these processes are monitored and controlled presently is based on ex-situ testing of wafer, chips, or structures. Within the process tool, fixed recipes are provided by tools and process suppliers. Run-by-run adjustments or control are based on external and delayed information on product performance or product yields. The sensors that are currently available are used in the fabs to monitor the conditions of fluid inside the process vessels and tanks, but far away from the inside of micro features (that is what needs to be monitored; it is also the bottleneck of cleaning and drying). The present monitoring techniques and devices do not provide realistic and accurate information on the cleanliness and condition of micro features.

Industry currently works around this problem while waiting for a solution; the process condition and cleaning and drying are often set with very large factors of safety (over-cleaning and over-rinsing). Large quantities of water and other chemicals are used (much more than what is really needed). This results in wasted chemicals and water, increased process time, lowered throughput, increased cost, and it causes reliability issues because of lack of process control.

SUMMARY OF THE INVENTION

The present invention provides a method of improving the clean, rinse and dry processes during the manufacture of ICs, MEMS and other micro-devices to conserve solution and energy while completing the process within a specified time.

This is accomplished using an electro-chemical residue sensor (ECRS) that monitors the remaining contamination while it is being removed from micro-features including surfaces or void micro features in the patterned wafers. The ECRS provides for in-situ and real-time measurement of residual contamination on a surface or inside void micro features within the sensor that represent a surface or micro features on production component(s) that need to be cleaned. The ECRS measures impedance, and so is very sensitive to the concentration of residual impurities on the surface and inside the micro feature. The measured impedance response of one or more surfaces or micro features within the ECRS, namely the magnitude and phase, any sharp transitions or leveling off provide in-situ information regarding the residual impurity concentrations and the status of the clean, rinse and dry processes. The in-situ measurements are used to design and optimize a production run and/or to monitor the production run in real-time to control the process conditions and transfer of a patterned wafer through the processes.

These and other features and advantages of the invention will be apparent to those skilled in the art from the following detailed description of preferred embodiments, taken together with the accompanying drawings, in which:

BRIEF DESCRIPTION OF THE DRAWINGS

FIGS. 8a and 8b are diagrams of a conventional rinse process and an ECRS-optimized rinse process;

DETAILED DESCRIPTION OF THE INVENTION

The present invention provides a method of optimizing the clean, rinse and dry processes during the manufacture of ICs, MEMS and other micro-devices to conserve solution e.g. cleaning solution, ultra pure rinse water or drying gas, and energy subject to completing each process within a time constraint. All high aspect ratio void structures such as vertical micro-features and buried micro-channels and micro-surfaces formed in or on a dielectric will be generally referred to as a 'micro feature' hereafter. Void micro features have a void space no greater than 10 microns and more typically 3 nm to 3 microns. A surface micro feature is no greater than 100 microns in width and typically 300 nm to 30 microns.

An electro-chemical residue sensor (ECRS) monitors either remaining contamination or contamination being removed from micro features formed in or on a dielectric film on the patterned wafers. The ECRS provides for in-situ and real-time measurement of residual contamination on or inside micro features within the sensor that represent micro features on production component(s) that need to be cleaned. The ECRS serves as a 'proxy' for the true conditions on or inside the micro-features of the production devices on the patterned wafer. The ECRS measures impedance, which is very sensitive to the concentration of residual impurities on the surface and inside the micro feature. The measured impedance response of one or more micro features within the ECRS, namely the magnitude and phase, any sharp transitions or leveling off provide in-situ information regarding the residual impurity concentrations and the status of the clean, rinse and dry processes. This information can be used to determine what process variables and specifically how process conditions affect the rate of change of the measured impedance. The in-situ measurements are used to design and optimize a production run and/or to monitor the production run in real-time to control the process conditions and transfer of a patterned wafer through the processes.

Cleaning, Drying and Rinsing Micro-Features

The cleaning of residue from a micro feature will typically be performed by a sequence of clean/rinse steps followed by a dry step. During a clean, the surface or micro feature is exposed to a cleaning chemical. The cleaning chemical removes residues and particles from the surface that may have formed there during prior processing. During the rinse, the surface or micro feature is exposed to ultra pure water. The water removes the cleaning chemical. During the dry, the surface or micro feature is exposed to a dry gas, such as dry air, isopropyl alcohol or nitrogen. The gas, sometimes in combination with heat or a spinning motion removes the remaining moisture.

Figure 1:
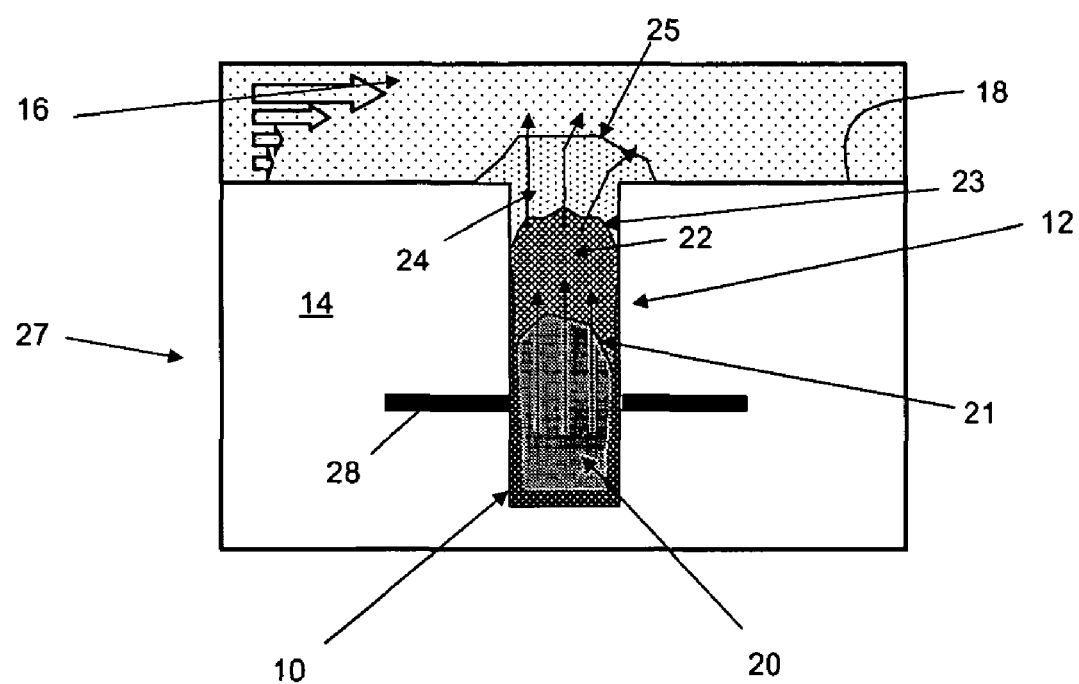
FIG. 1 is a diagram of the removal of a surface layer of unwanted residue from a vertical micro feature showing the concentration profile of the removed residue inside the micro feature.

FIG. 1 illustrates the removal process of a film of residue 10 from a void micro feature 12 in a dielectric film 14. The residue is slowly removed by a cleaning fluid, which in turn becomes contaminated by the residue. In the bulk 16 of the fluid, away from the surface 18, the fluid flows briskly and there is a very low concentration of residue in the bulk fluid. Conventional processes monitor the contamination in the bulk of the fluid. Since the transport of the active components of the cleaning fluid into the feature or the transport of the residue out of the feature is slow relative to the removal of the residue from the reactor once it is present in the bulk of the fluid, the removal of residue will progress from the top of the feature to the bottom. Consequently, the concentration of residue in the cleaning fluid is highest at the bottom of the micro feature and gets progressively lower closer to the surface, at which residue exits the micro feature. The regions 20, 22 and 24 bounded by lines with equal concentration of residue 21, 23 and 25 have concentrations of residue that progressively decrease as the region is closer to the surface at which the residue exits the micro feature. The removal of the ultimate traces of residue will occur last at the bottom of the smallest micro features. The cleaning of these areas are the bottleneck of the process. When the feature is being rinsed with ultra pure water to remove the cleaning fluid, the cleaning fluid will likewise be rinsed last from the bottom of the micro features. When the feature is being dried to remove the rinse water, the moisture will likewise be removed last from the bottom of the micro features. In conventional processes with conventional monitoring, sensors measure the bulk properties of the fluid away from the surface in which there is a very low concentration of residue. Therefore, the conventional monitoring does not provide an accurate representation of the contamination of the micro features. In the present invention, an ECRS 27 includes a pair of electrodes 28 formed in dielectric film 14 on opposite sides of void micro feature 12 to measure the impedance inside the micro feature to provide an accurate representation of the remaining contamination albeit residue, cleaning solution or water.

The physical mechanisms that are responsible for the progression, and that limit the rate of progression of the removal of cleaning chemical during the rinse of a surface 30 containing multiple micro features are illustrated in FIGS. 2a-2d. A vertical micro feature 32, buried microchannel 34 and micro surface 36 are formed in or on dielectric film 38. An ECRS 39 is configured with pairs of electrodes 40, 42 and 44 formed on opposite sides of the respective micro features to measure the impedance during the processes in order to monitor the residual concentration of cleaning chemical inside a vertical micro feature, inside a horizontal micro feature or at the surface as the process progresses.

Figure 2A:
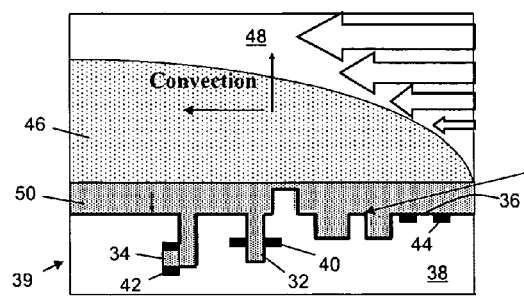
FIGS. 2a through 2d are cross section views of the surface at various stages during removal of a surface layer of unwanted residue showing the specific physical processes that affect the contamination removal rate.
Figure 2B:
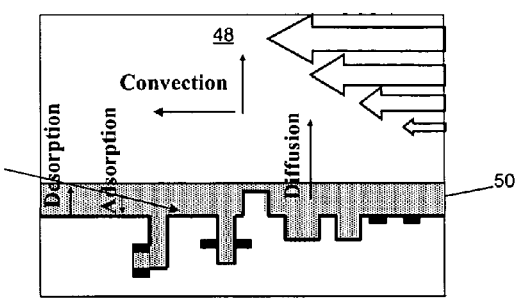
Figure 2C:
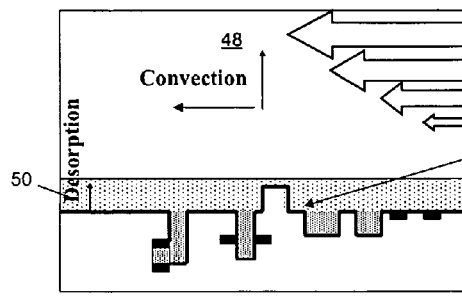
Figure 2D:
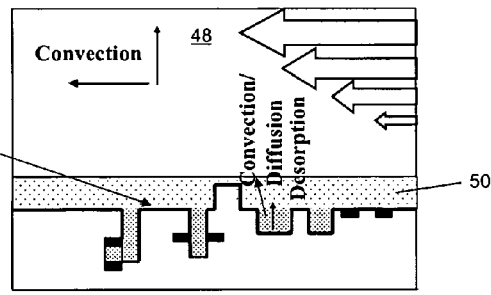

Initially, a leaning chemical carryover layer 46 is washed away by the rinse water 48 through the process of fluid mixing and motion called convection as shown in FIG. 2a. This process initially does not remove a surface layer 50 close to surface 30 where there is no or very little rinse water motion. When the carryover layer has been removed, the cleaning chemical is released from the surface by desorption into the surface layer and slowly diffuses away from the surface into the rinse water flow. Because the concentration of cleaning chemical in surface layer 50 is still high as shown in FIG. 2b, the cleaning chemical can re-adsorb onto surface 30. As the concentration of cleaning chemical on the surface drops as shown in FIG. 2c, adsorption ceases to play a role and the desorption rate from the surface dominates the removal rate. When the surface concentration of cleaning chemical has dropped sufficiently, removal of the cleaning chemical from the micro features 32 and 34 becomes rate limiting. The physical processes repeat themselves inside the micro features as shown in FIG. 2d.

Figure 3A:
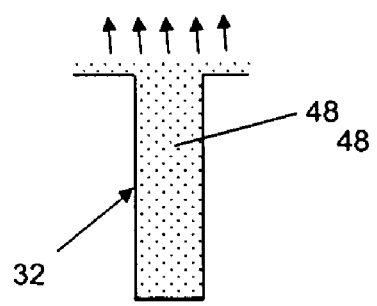
FIGS. 3a-3c are diagrams illustrating the specific physical processes for the dry process.
Figure 3B:
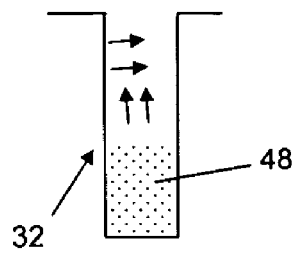
Figure 3C:
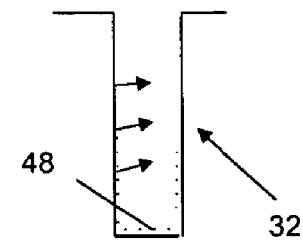

The physical mechanisms that are responsible for the progression, and that limit the rate of progression of the removal of rinse water 48 during the drying of surface including micro feature 32 are illustrated in FIGS. 3a-3c. As shown in FIG. 3a, initially the predominant mechanism is surface drying from the top surface of the dielectric film. Once the main surface is dry, axial and radial drying inside micro feature 32 will occur as shown in FIG. 3b. Once the volume of the micro feature is dry, any remaining moisture will be removed via desorption from the side walls of the feature as shown in FIG. 3c.

For cleaning applications, the presence of a surface deposit will impact the impedance between the electrodes since it can hinder or help the conduction process or can have a different dielectric constant than the cleaning fluid. For rinsing applications, the presence of ionic contaminants in ultra pure water changes the resistivity of the water even if very small concentrations (parts per billion level) are present. Therefore, the impedance measured between two electrodes will depend very much on the conductivity of the fluid and thus the presence of ions. Even non-ionic impurities, directly and through interactions with other species present, change the dielectric properties and surface response to ions inside the micro feature, which in turn define the impedance. Therefore it can be possible to determine during the rinse process that the chemical clean was not sufficiently effective in removing the surface deposits during the cleaning process. For drying applications, the removal of the water from the micro feature (replacing it with dry air, pure nitrogen or some other gas) will likewise result in a measurable change in impedance, since the difference between the conductivity of ultra pure water and gas can easily be detected. Conduction along sidewalls can be measured, so that the amount of moisture adsorbed on the sidewalls or (slightly) conducting residual impurities on the sidewalls will be detected.

Figure 4:
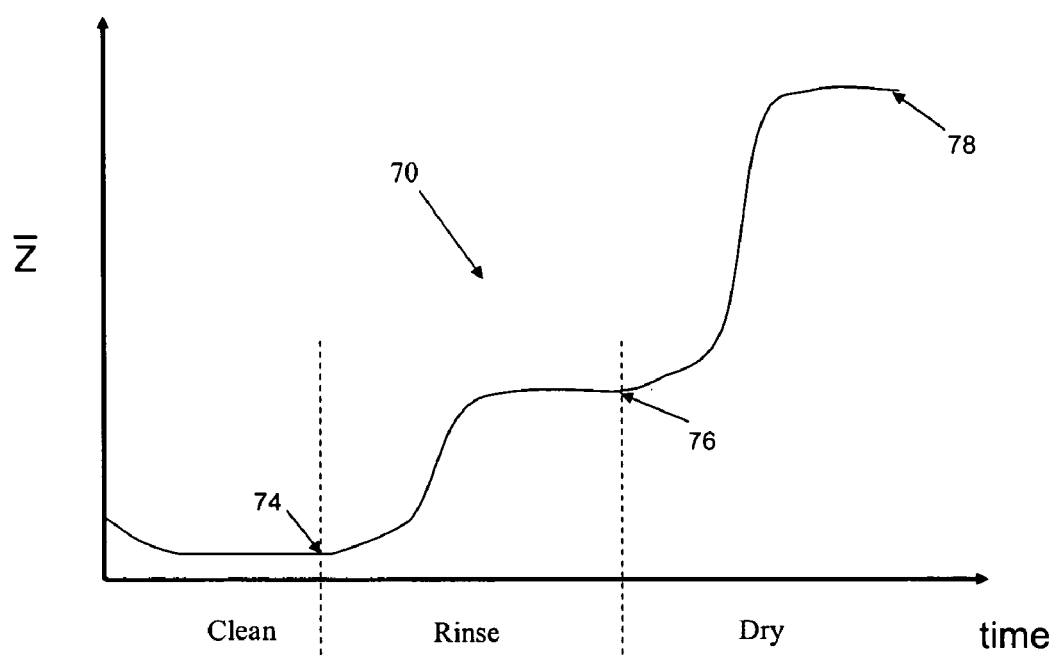
FIG. 4 is a plot of impedance vs. time for a representative clean/rinse/dry cycle.

An exemplary impedance response 70 for a vertical micro feature is depicted in FIG. 4. The physical mechanisms responsible for the progression within and through the clean, rinse and dry processes are evident from the impedance response. The cleaning process removes residue from the micro feature thereby reducing the impedance along a gradient as the concentration of residue is reduced eventually leveling off at an endpoint impedance value 74 representative of a clean feature immersed in the cleaning chemical. The rinse process initially removes the carryover and surface layers producing a gradual increase in impedance. Once convection and diffusion become effective to remove the cleaning solution from inside the micro feature, the impedance increases sharply. Once all of the cleaning solution has desorbed from the walls of the micro feature, the impedance levels off to an endpoint 76 representative of a rinsed feature immersed in ultra pure water. Similarly, the dry process initially removes water from the surface producing only a gradual increase in impedance inside the feature. Once axial and radial drying become effective to remove moisture from inside the micro feature, the impedance increases sharply again. Once all of the water has desorbed from the walls of the micro feature, the impedance levels off at an endpoint 78 representative of a dry feature.

For a given production process (specified process conditions for a number of process variables), the ECRS can be used to monitor the processes and determine the endpoint times 74, 76 and 78 for the clean, rinse and dry process, respectively. Alternately, the ECRS could be used during a production run to detect the endpoint impedances, terminate each process and transfer the production wafers to the next process. The ECRS could also be used to detect changes in the impedance to control certain process conditions in order, for example, to reduce the amount of solution or energy consumed during a given process.

Production Process Design Optimization Using an ECRS

More interestingly, the rate at which the impedance changes, which is a direct indicator of the rate at which contaminants are removed from the micro feature, may be dependent or independent of the selected process conditions for different process variables. Measurement of the impedance for a range of process conditions for the different processes and sub-processes can determine whether and to what extent the rate is dependent upon certain process conditions. This information can than be used to determine a low resource solution for each process or sub-process that perform the requisite function within a prescribed time constraint. The low resource solution is suitably optimized for some combination of the amount of solution use and energy expended during each process and for the entire process.

Figure 5:
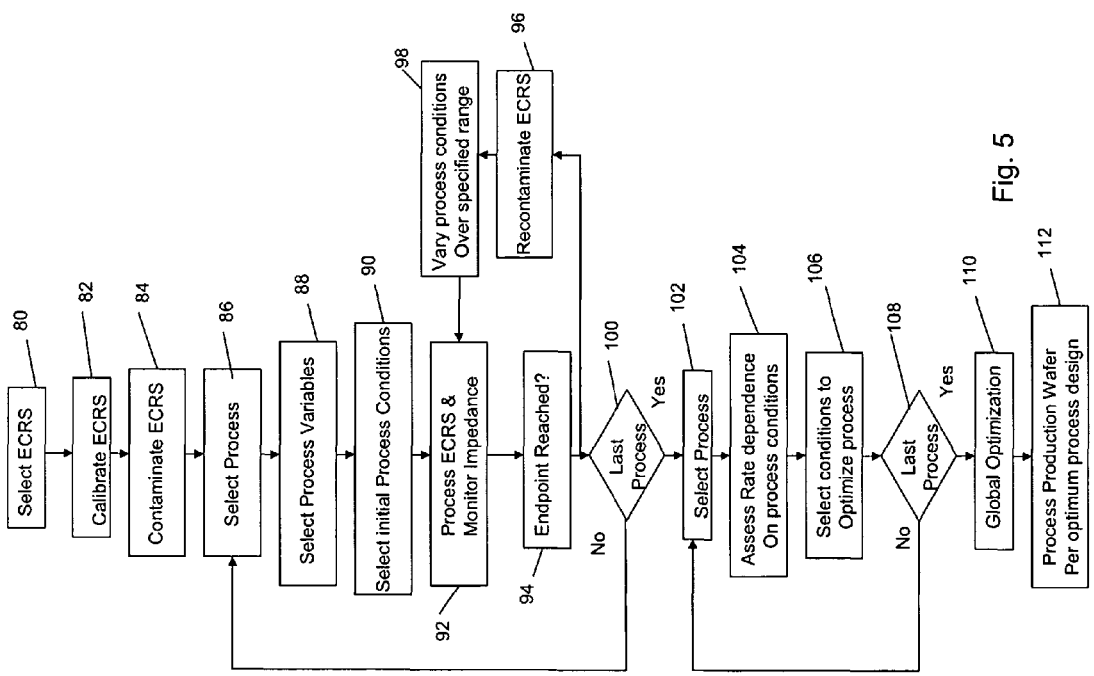
FIG. 5 is a flowchart for using an ECRS to design an optimized clean/rinse/dry process.

An exemplary process for using the ECRS to design and optimize a production process for cleaning, rinsing and drying production wafers is illustrated in FIG. 5. The first step is to select an ECRS (step 80) for a particular production wafer. The ECRS may include different micro features selected from vertical, buried microchannel and surface features and may include multiple different geometries for each in order to provide the impedance measurements necessary to accurately characterize the processes for the production wafers. The ECRS is calibrated (step 82) for each process subject to design optimization. This is accomplished by measuring the impedance of the ECRS in a known solution e.g. the cleaning solution, ultra pure rinse water or drying gas. The ECRS is then contaminated to imitate the production process (step 84). For example, if design optimization is performed on the cleaning process, the ECRS is contaminated with residue that would imitate the last step in the etching and release steps. If design optimization is skipping the cleaning process, the ECRS may be contaminated with cleaning solution. Design optimization can be performed on any one, two or all of the processes. In addition, the clean and rinse processes are typically repeated a few times and each may be optimized individually.

The next process to be optimized is selected (step 86). The overall process and each clean/rinse/dry process have a number of parameters. Some of these parameters such as reactor size and shape are fixed, others such as flow rates, temperature, solution composition and spin rates are variable and some such as a specified time constraint to complete the process or specified temperature required at the end of a particular process may be considered fixed or variable. The process variables to be investigated and their initial process conditions are selected (steps 88 and 90).

The ECRS is subjected to specified process conditions and the impedance of the one or more micro features is monitored (step 92) until the calibrated endpoint impedance is reached (step 94). The ECRS is recontaminated (step 96), the process conditions are varied over a specified range (step 98) and steps 92 and 94 are repeated until the endpoint is again reached. For example, the clean process may be tested with cleaning solutions having different chemical concentrations at different temperatures. Higher concentrations and temperatures generally being more effective to clean the devices but requiring more expensive chemicals and energy and generating more waste. The rinse process may be tested using different flow rates and temperatures. Similarly higher flow rates and temperatures being generally more effective but also more resource intensive. Finally, the dry process may be tested using different spin rates and temperatures. Steps 92, 94, 96 and 98 are repeated at least once and perhaps multiple times for each process variable for the investigated process. When complete, if there is another process (step 100) to investigate control returns to step 86.

Once all the impedance data has been measured for the processes, the data is used to design the individual processes and perhaps the overall process and suitably to optimize the process to conserve resources. The processes are generally not independent of each other. For example, the chemical concentration, immersion temperature and effectiveness of the clean process can impact the rinse process. These interdependencies should be considered when designing each process.

For the next selected process (step 102), for each process variable that was monitored the dependence of the rate of change of the impedance on process conditions is assessed (step 104). This determines whether the rate is dependent or independent of process condition, how strongly and whether that dependency changes during the process. Based on this rate dependency information for the one or more process variables, process conditions to be used in production are selected to provide a low resource solution (step 106).

The low resource solution is generally subject to the constraint of performing the function of the process (i.e. reaching the corresponding endpoint impedance) within a specified time constraint. Alternately, the time can be treated as a variable for optimization. Other constraints such as min/max flow rates, min/max temperatures, min/max processing times etc. may also be placed on the solution based on other considerations such as capabilities of the cleaning system, protection of the wafer or dependencies of other processes. The optimized low resource solution can be determined by or with the aide of a computer programmed to consider the different variables and constraints and the cost of different conditions (solution, energy, time). The steps are repeated until the last process has been designed (step 108).

At this point, the process designer (or computer) may assess the overall process to consider the process dependencies or any other higher level considerations (step 110). These process dependencies could also be considered as constraints on the individual processes and incorporated as each is designed. The result is a production process in which at least one process has been designed to provide a low resource solution. Thereafter, lots of production wafers are cleaned/rinsed/dried using the optimized production process step 112).

Clean Process

Figure 6A:
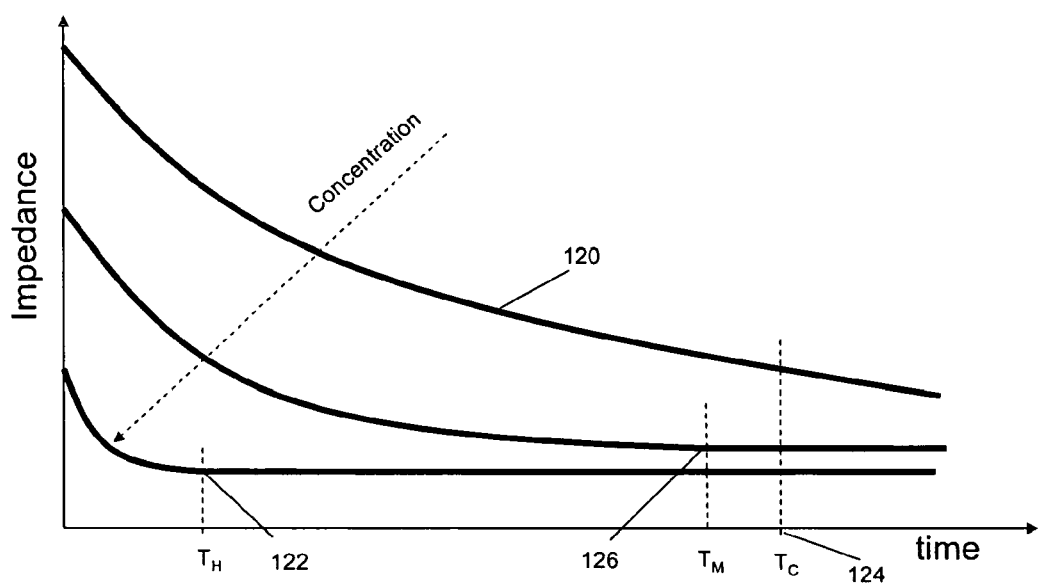
FIGS. 6a and 6b are impedance plots illustrating the dependence of the clean process on process conditions for cleaning chemical concentration and temperature.
Figure 6B:
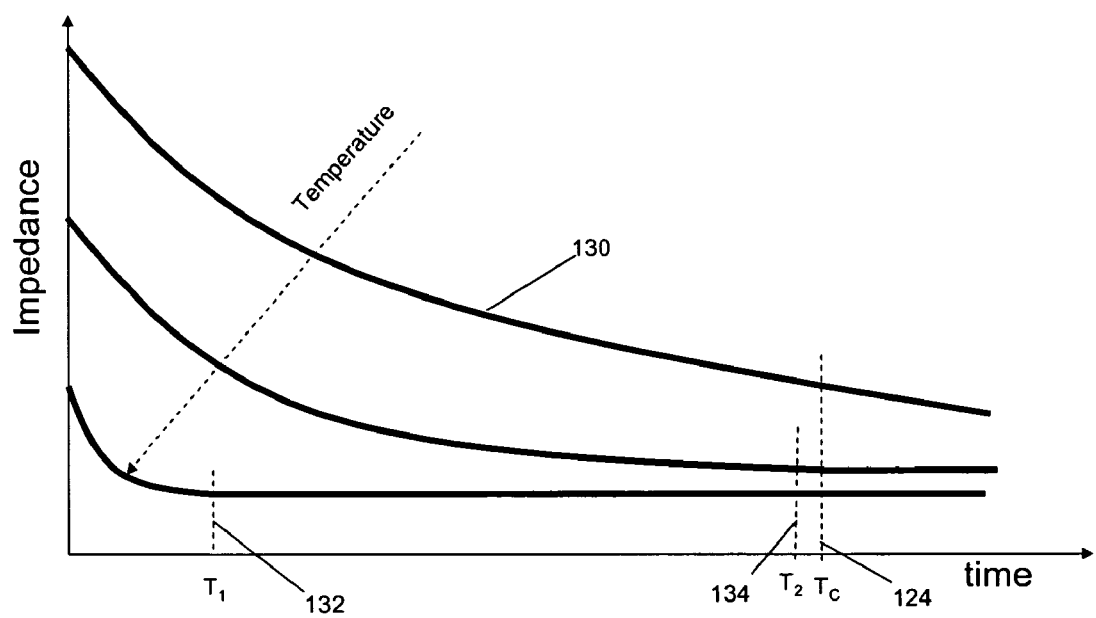

The performance and rate of the clean process is dictated by the process conditions for the chemical concentration of the cleaning solution and the temperature of the immersion bath. As shown in FIG. 6a, the rate of change of impedance response 120 increases with increasing chemical concentration. As a result, the high concentration solution reaches the endpoint impedance at a time $T_H$ 122 well in advance of the specified time constraint $T_C$ 124 whereas the medium concentration solution reaches completion at a time $T_M$ 126 near the specified constraint and the low concentration does not finish the clean process within the prescribed time limit. As shown in FIG. 6b, the rate of change of impedance response 130 increases with increasing temperature. As a result, the high temperature bath reaches the endpoint impedance at a time $T_1$ 132 well in advance of the specified time constraint $T_C$ 124 whereas the medium temperature bath reaches completion at a time $T_2$ 136 near the specified constraint and the low temperature bath does not finish the clean process within the prescribed time limit.

The dependency of the clean process on the chemical concentration and temperature as reflected in these plots is assessed and a low resource solution that reaches the endpoint impedance within and preferably near time constraint $T_C$ is selected. For example, a medium concentration solution at medium temperature conserves chemicals and energy while satisfying the constraints. It is important to note that without the precise impedance measurements over a range of process conditions to determine these dependencies a conventional clean would typically use high concentration chemicals at high temperatures to ensure an effective clean in the prescribed time, thus wasting resources.

Rinse Process

The performance and rate of the rinse process is dictated by the process conditions for the flow rate of the ultra pure water rinse solution and the temperature of the solution. As will be illustrated, the rate dependency on each of these process conditions changes during the rinse process creating additional opportunities for resource optimization.

Figure 7A:
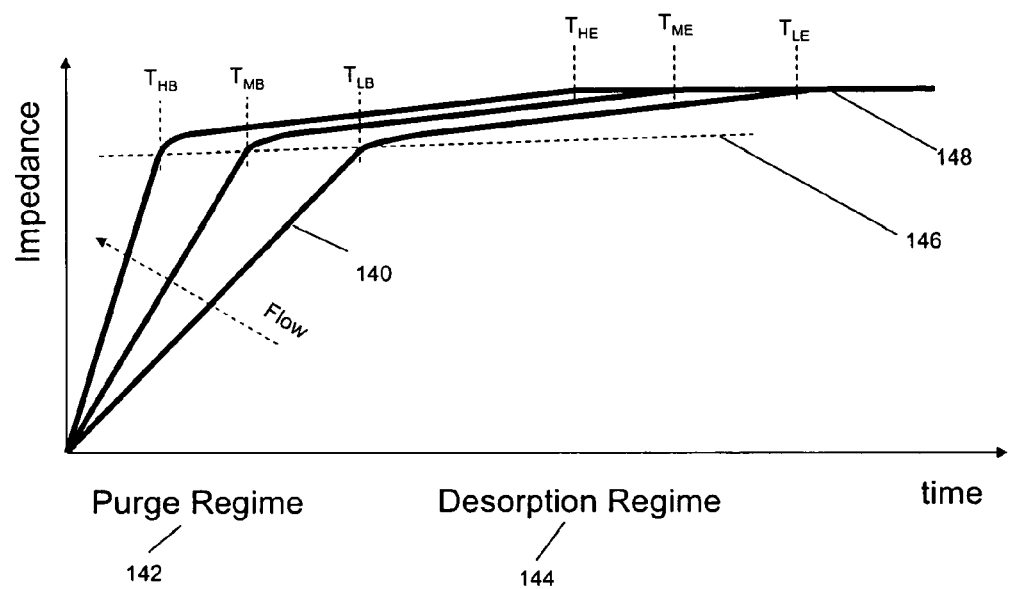
FIGS. 7a and 7b are impedance plots illustrating the dependence of the rinse process on process conditions for water flow rate and temperature.

As shown in FIG. 7a, the rate of change of impedance response 140 increases with increasing flow rate during an initial purge regime 142 but is largely independent of flow rate during a subsequent desorption regime 144. The different regimes are demarcated by a breakpoint impedance 146 below which the clean up rate is dependent on flow rate and above which the rate is not dependent on flow rate.

As a result, the high flow rate rinse reaches the breakpoint impedance at a time $T_{HB}$ before the medium and low flow rate rinses at times $T_{MB}$ and $T_{LB}$, respectively. It follows that the high flow rate rinse also reaches the endpoint impedance 148 at a time $T_{HE}$ before the medium and low flow rate rinses at times $T_{ME}$ and $T_{LE}$, respectively. However, because the desorption rate is independent of flow rate the overall time difference is dictated solely by the rate in the purge regime. A low resource solution may use a high flow rate during the purge regime and transition to a low flow rate during the desorption regime.

Figure 7B:
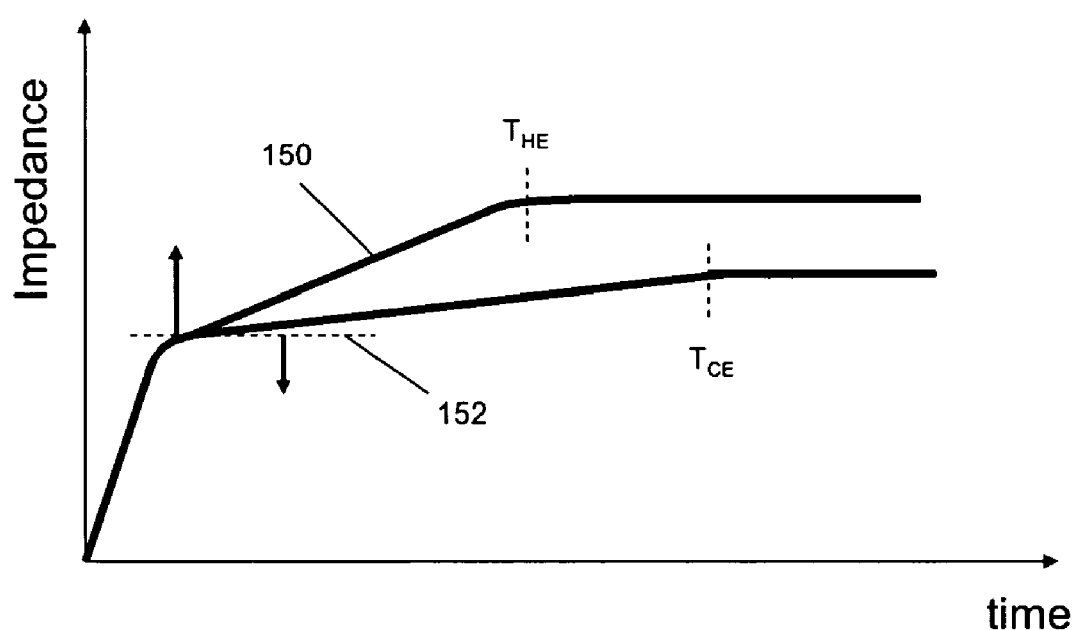

As shown in FIG. 7B, the rate of change of impedance response 150 is independent of rinse temperature during an initial flush of the tank but increases with temperature during a subsequent desorption regime demarcated by breakpoint impedance 152. The demarcation roughly corresponds to the purge and desorption regime for flow rate; during the purge the rinse is temperature independent but not so during desorption. As a result, the hot rinse reaches the endpoint impedance at a time $T_{HE}$ before the cold rinse at $T_{CE}$. Note the endpoint impedance varies with the temperature of the rinse, which must be considered during calibration. A low resource solution may use a cold rinse initially and transition to a low flow rate during the desorption regime.

The dependency of the rinse process on the flow rate and temperature as reflected in these plots is assessed and a low resource solution that reaches the endpoint impedance within and preferably near a time constraint is selected. It is important to note that without the precise impedance measurements over a range of process conditions to determine these dependencies a conventional rinse would typically use a high flow rate hot rinse 160 for several minutes followed by a high flow cold rinse 162 (to cool the wafer) and then idle flow 164 to ensure an effective rinse in the prescribed time, thus wasting resources as shown in FIG. 8a. By contrast an optimized low resource solution might include a high flow cold rinse 166 during the purge regime, a short high flow hot rinse 168 at the end of the purge regime to heat the rinse tank and then a low flow hot rinse 170 during the desorption regime. A short high flow cold rinse 172 is used to cool the wafers followed by idle flow 174. The total rinse time is unchanged in this example but the total quantity of water and the energy required have been reduced dramatically. In this example, approximately 15 gallons of cold water and 70 gallons of hot water are saved per cycle.

Dry Process

The performance and rate of the dry process is dictated by the process conditions for the spin velocity of the wafer and the temperature and flow velocity of the dry gas. As will be illustrated, the rate dependency on each of these process conditions changes during the rinse process creating additional opportunities for resource optimization.

Figure 9A:
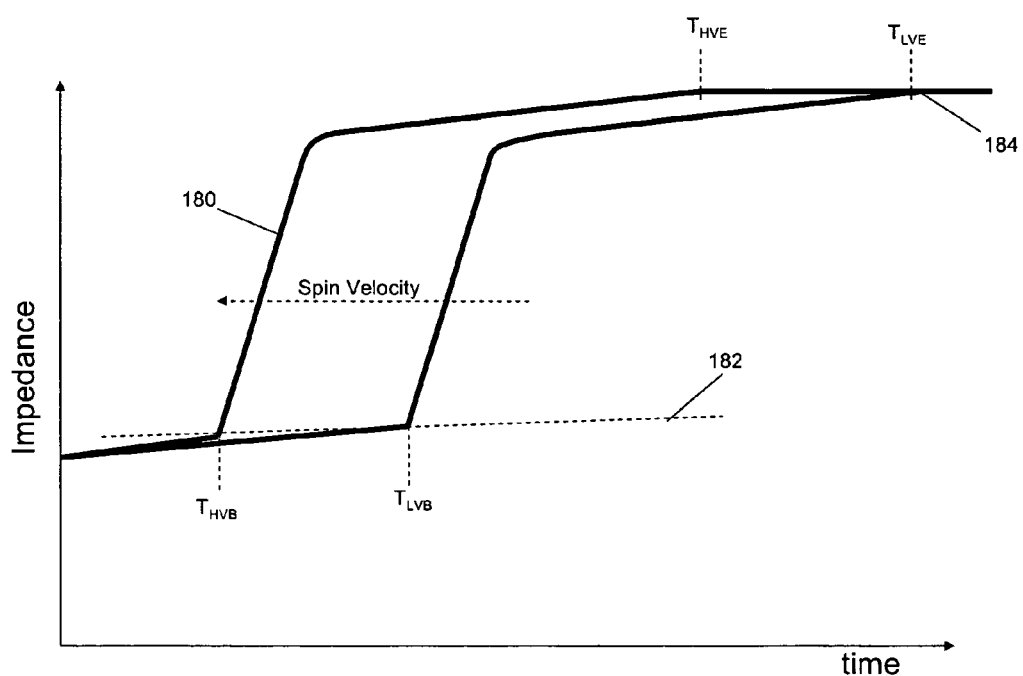
FIGS. 9a and 9b are impedance plots illustrating the dependence of the dry process on process conditions for spin rate and temperature.

As shown in FIG. 9a, the rate of change of impedance response 180 increases with increasing spin velocity or gas flow rate during an initial surface drying regime but is largely independent of spin velocity or gas flow rate during a subsequent desorption regime. The different regimes are demarcated by a breakpoint impedance 182 below which the clean up rate is dependent on spin velocity or gas flow rate and above which the rate is not dependent on flow rate.

As a result, the high spin velocity rinse reaches the breakpoint impedance at a time $T_{HVB}$ before the low velocity rate rinses at time $T_{LVB}$. It follows that the high velocity rate rinse also reaches the endpoint impedance 184 at a time $T_{HVE}$ before the low velocity rate at time $T_{LVE}$. However, because the desorption rate is independent of spin velocity or gas flow rate the overall time difference is dictated solely by the rate in the surface drying regime. A low resource solution may use a high spin velocity for surface drying and transition to a low spin velocity during the desorption regime.

Figure 9B:
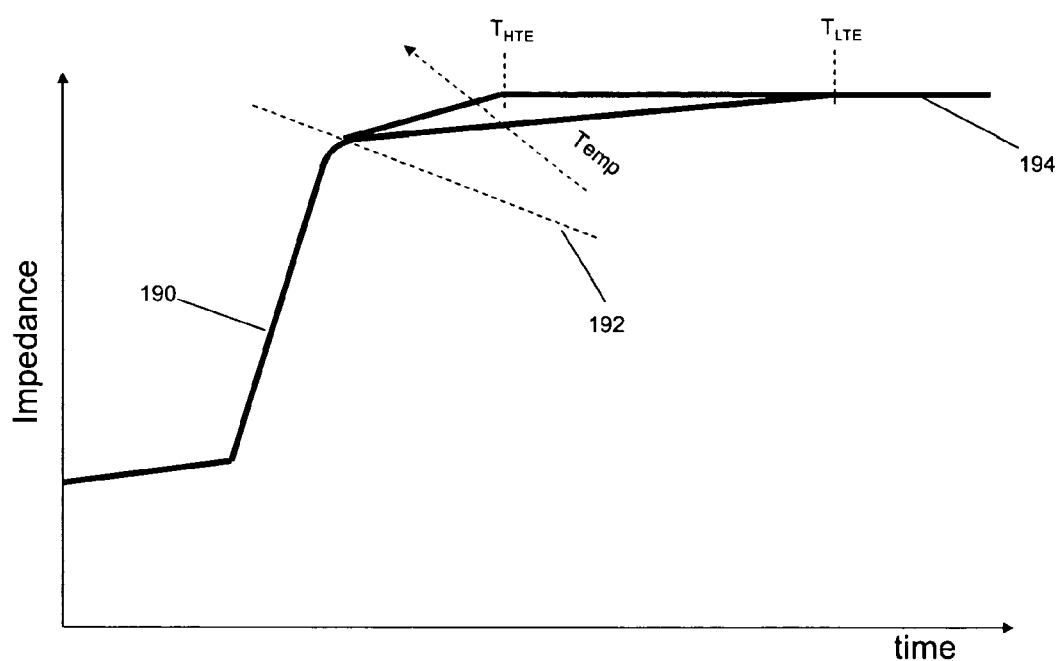
Figure 10A:
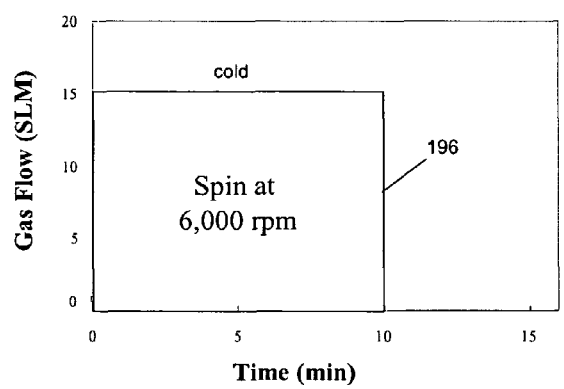
FIGS. 10a and 10b are diagrams of a conventional dry process and an ECRS-optimized dry process.
Figure 10B:
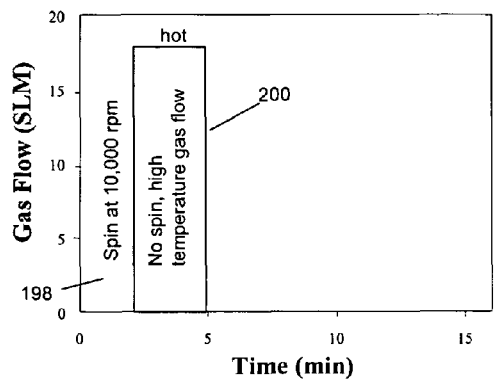

As shown in FIG. 9b, the rate of change of impedance response 190 is not strongly dependent on temperature during the surface drying regime but increases with temperature during the subsequent desorption regime demarcated by a breakpoint impedance 192. As a result, the high temperature dry reaches the endpoint impedance 194 at a time $T_{HTE}$ before the low temperature at time $T_{LTE}$. A low resource solution may use a low temperature gas for surface drying and transition to a high temperature gas during the desorption regime.

The dependency of the dry process on the spin velocity and temperature as reflected in these plots is assessed and a low resource solution that reaches the endpoint impedance within and preferably near a time constraint is selected. It is important to note that without the precise impedance measurements over a range of process conditions to determine these dependencies a conventional dry would typically use a moderate spin (6,000 rpm) cold gas 196 for 10 minutes to ensure an effective dry as shown in FIG. 9a. By contrast an optimized low resource solution might include a high spin (10,000 rpm) cold gas 198 for a couple minutes for surface drying and then a no spin hot rinse 200 for a couple minutes for desorption cutting the dry cycle time in half.

Production Wafer Processing and Monitoring

Figure 11A:
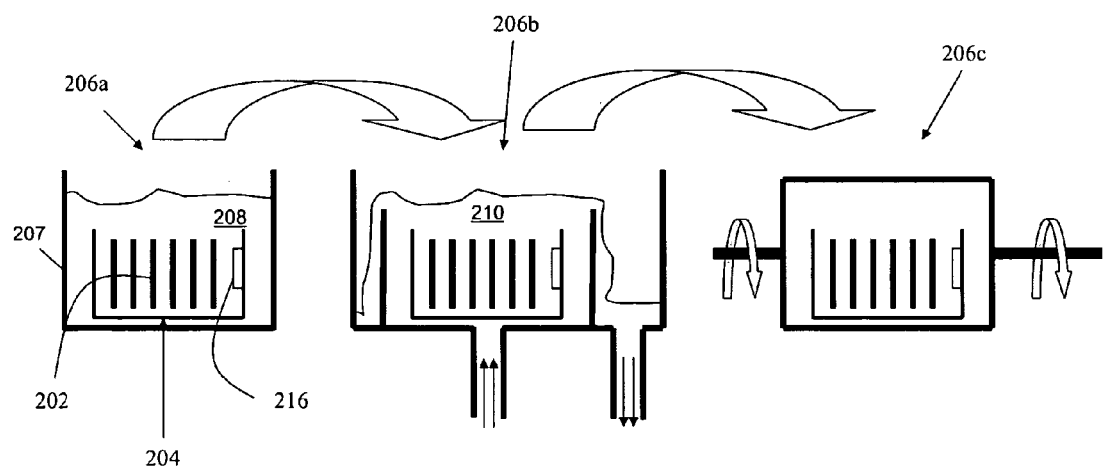
FIGS. 11a and 11b are diagrams illustrating the clean/rinse/dry processes.
Figure 11B:
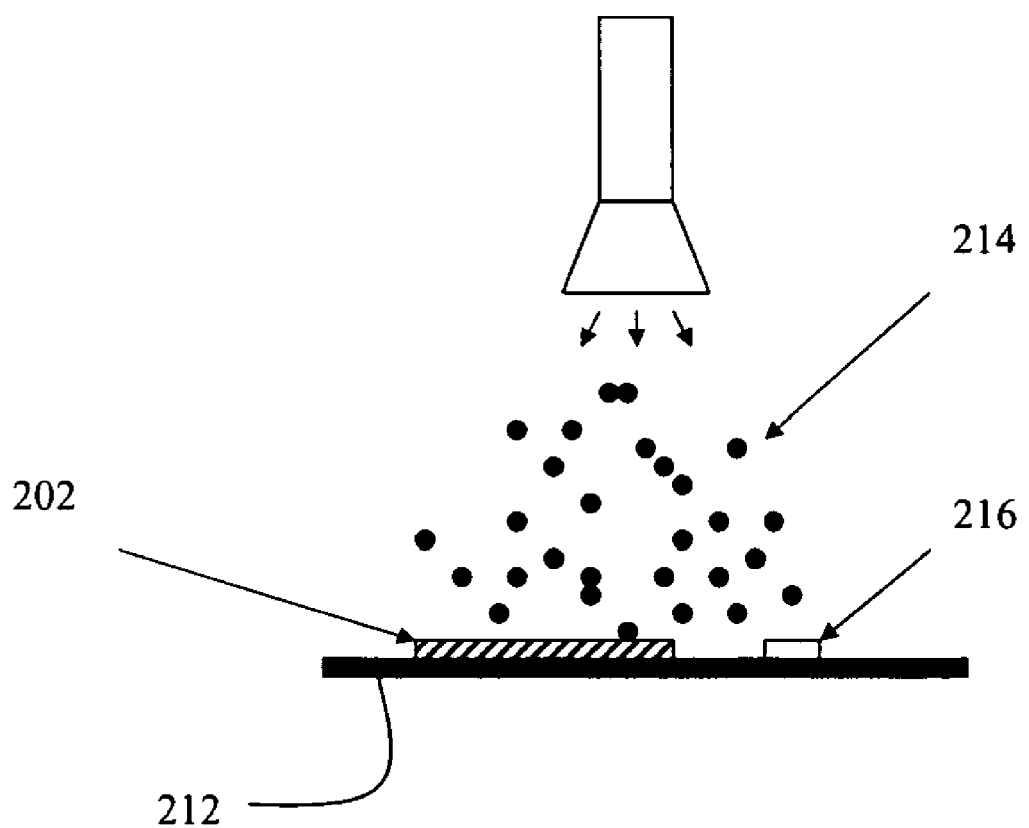

To process production wafers in accordance with the low resource solution, a number of production wafers 202 are inserted into a cassette 204 and processed through a sequence of clean/rinse/dry baths 206a-206c in a tank 207 as shown in FIG. 11a. The concentration and temperature of cleaning solution 208, flow rate and temperature of the rinse solution 210, and spin velocity and temperature of the dry gas are controlled in accordance with the production process. Alternately, a single production wafer 202 can mounted on a chuck 212 subjected to a sequence of clean/rinse/dry sprays 214 as shown in FIG. 11b. In either case, the production processes can be operated with or without an ECRS 216. The ECRS can be used to either monitor the impedance of the production process to provide feedback to make additional refinements to the process offline or to provide real-time data to control the process in some manner.

Figure 12:
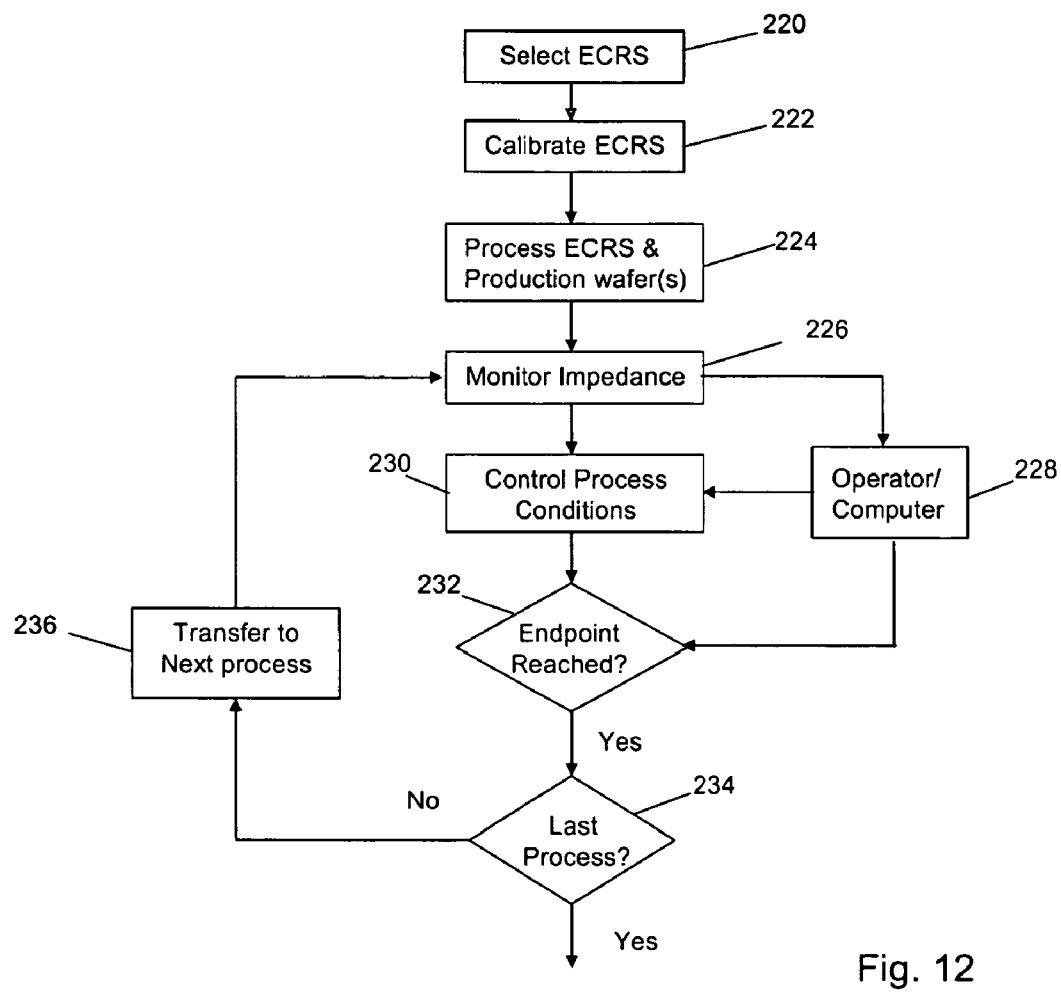
FIG. 12 is a flowchart for using an ECRS to monitor and control a clean/rinse/dry process.

As illustrated in FIG. 12, the ECRS could be used to monitor the impedance in order to control process conditions or to terminate each process and transfer the production wafer(s) to the next process. An appropriate ECRS is selected (step 220), calibrated (step 222) and processed with the production wafers (step 224) to monitor the impedance of the micro feature(s) in-situ in real-time (step 226). An operator or computer 228 monitors the impedance levels and rates of change and uses the information to control process conditions (step 230) and/or determine when the process endpoint has been reached (step 232). For example, the ECRS could be used to control when the rinse transitions for cold-to-hot or high-to-low flow or when the dry transitions from high spin velocity to low spin velocity. Once the endpoint is reached, if the current process is not the last process (step 234) the wafers are transferred to the next process (step 236) and the process continues.

Real-time in-situ monitoring with the ECRS can be used to refine a low resource optimized solution or can be used with non-optimized solutions. In some situations, a manufacturer may not have the capability or choose not to optimize the production process. Instead the manufacturer may choose a conservative process that ensures cleaning but is wasteful of resources and use the impedance data from the ECRS to control process conditions and transfer of the wafers to save resources where possible.

ECRS Configurations

The ECRS includes one or more micro features that represent micro features in micro devices fabricated on the production wafers and means to measure the impedance of the one or more micro features. This means includes at least a pair of electrodes on opposite sides of the micro feature and an impedance analyzer that applies an ac measurement signal between the electrodes to measure the impedance of the micro-feature. The means may also include one or more buffers that supply current to one or more conductive guards so that the guard voltage closely tracks the ac measurement signal voltage to reduce the effects of parasitic capacitance. As described previously, a 'micro-feature' may constitute a vertical void structure, a buried micro-channel or a surface. Configurations of exemplary ECRS for each are described below in reference to FIGS. 13 to 15.

ECRS for Vertical Void Micro-features

Figure 13A:
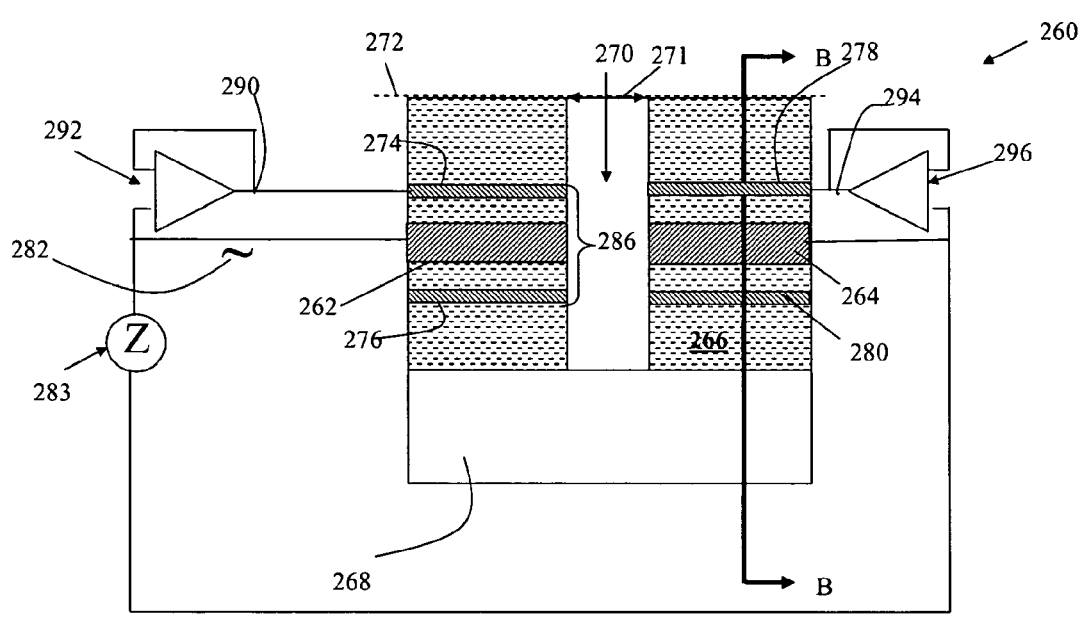
FIGS. 13a-13b are section views of an embodiment of an ECRS for monitoring vertical micro-features.
Figure 13B:
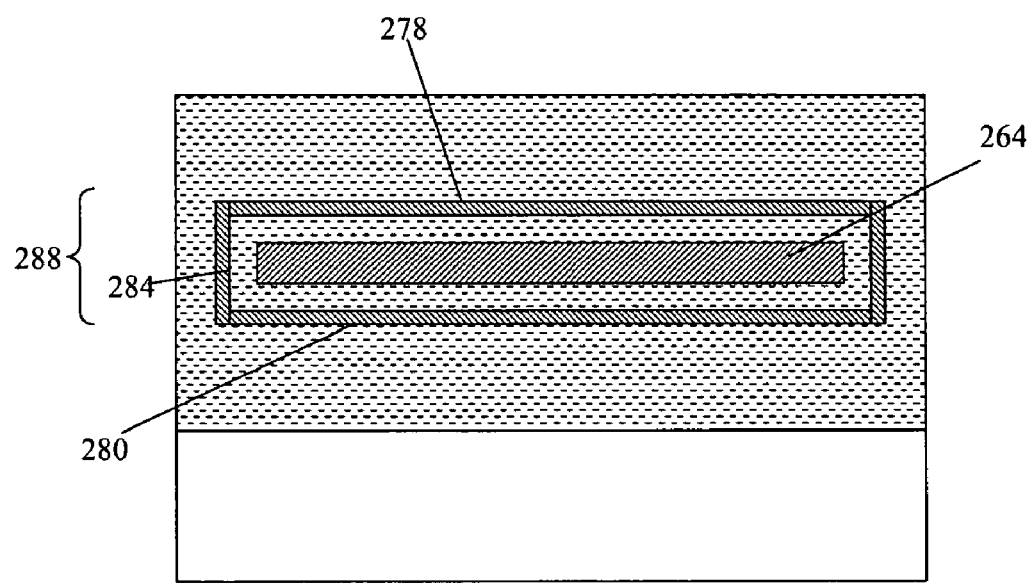

As shown in FIGS. 13a and 13b, an ECRS 260 includes a pair of electrodes 262 and 264 in a dielectric 66 on a substrate 68 on either side of a vertical void micro feature 270 having an opening 271 that lies in the plane of the fluid-solid interface 272. As shown, the micro feature is suitably oriented substantially perpendicular to the fluid-solid interface 272 and the dielectric stack. Conductive layers 274, 276 and 278, 280 lie above and below electrodes 262 and 264, respectively, on either side of micro feature 270 and the conductors (not shown) that carry the measurement signal 282, which is supplied by the impedance analyzer 283 via buffer 292 to the electrodes (such as a coaxial cable). A conductive perimeter 284 on either side of electrode 262 electrically connects layers 274 and 276 to form a guard 286. Similarly the conductive perimeter 284 on either side of electrode 264 electrically connects layers 278 and 280 to form a guard 288. The guards effectively surround their electrodes except at the edges of the micro feature and at the electrode contacts and electrically shield the electrodes from the surrounding environment.

The guard 286 is suitably connected to the output 290 of a guard buffer 292 that ensures that the guard is always at nearly the same voltage as electrode 262. Similarly, guard 288 is suitably connected to the output 294 of a guard buffer 296 that ensures that the guard is always at nearly the same voltage as electrode 264. The guards are only used to shield the electrodes from the rest of the environment and do not otherwise contribute to the measurement. The current required to make the guard voltage the same as the electrode voltage is supplied by buffers 292 and 296, not by the impedance analyzer 283, hence it does not distort the measurement signal 282. Each guard buffer has a first input connected to opposite sides of the impedance analyzer and a second input connected to a buffer output. The buffers have unity gain bandwidth larger than the ac measurement signal frequency to supply the requisite current to the guards.

The AC measurement signal 282 is applied between the two electrodes 262 and 264 and the impedance is measured by the impedance analyzer 283 as the ratio and phase difference between the measurement signal voltage and current. During monitoring, the change in monitor impedance is an indication of chemical removal/addition from the micro feature 270 or of motion of a chemical species inside the micro feature. The measured device impedance is related to the concentration inside the micro feature or to the surface concentration inside the pores of the dielectric film 266, thereby producing a concentration-versus-time profile. With the inclusion of the guard, the effective parasitic capacitance is sufficiently small to allow an electrical measurement of the total impedance between the electrodes to resolve $R_{sol'n}$ and/or $C_{dl}$.

The guards do not necessarily need to completely surround the electrodes. It may be sufficient for guards to include only conductive layers that lie above and below the electrodes (no conductive perimeter). Furthermore, a single guard that lies either above or below the electrode may be adequate in some cases.

ECRS for Buried Micro-Channels

Figure 14A:
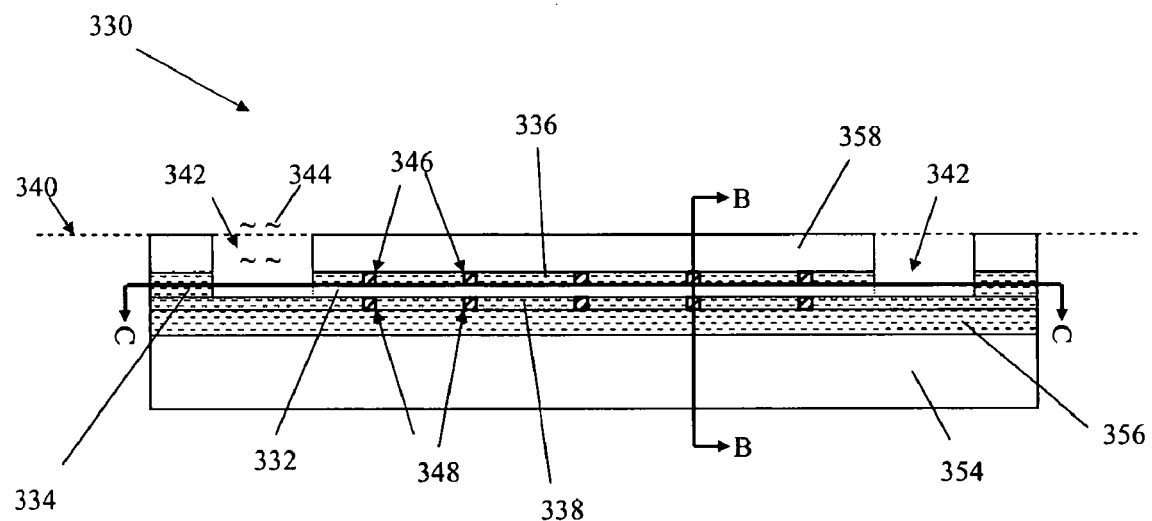
FIGS. 14a-14c are section views of an embodiment of a ECRS for monitoring buried micro-channels.
Figure 14B:
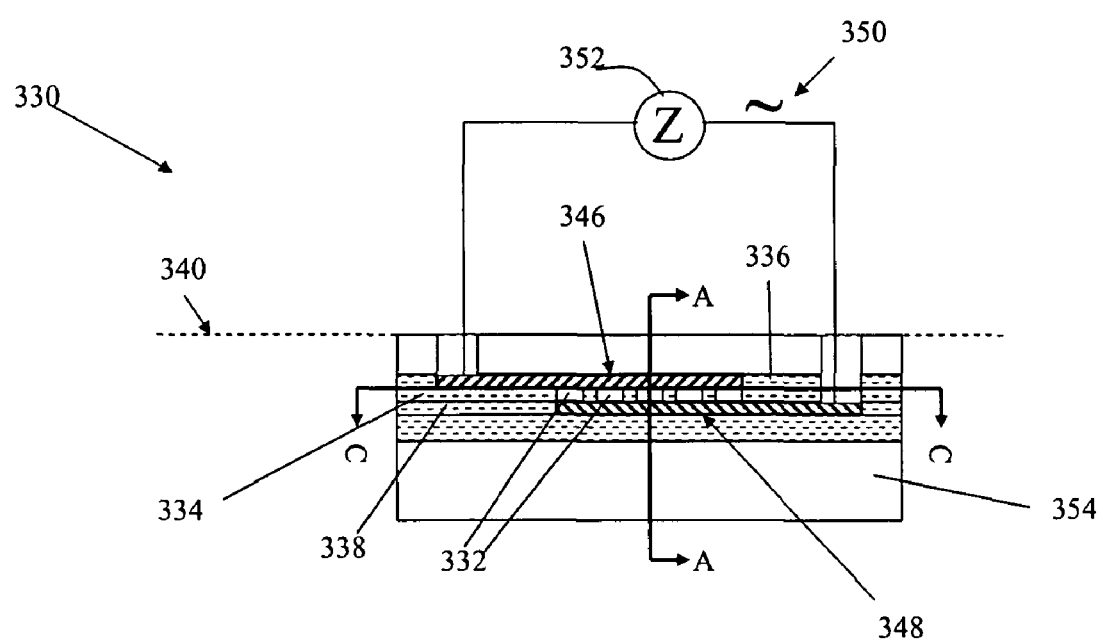
Figure 14C:
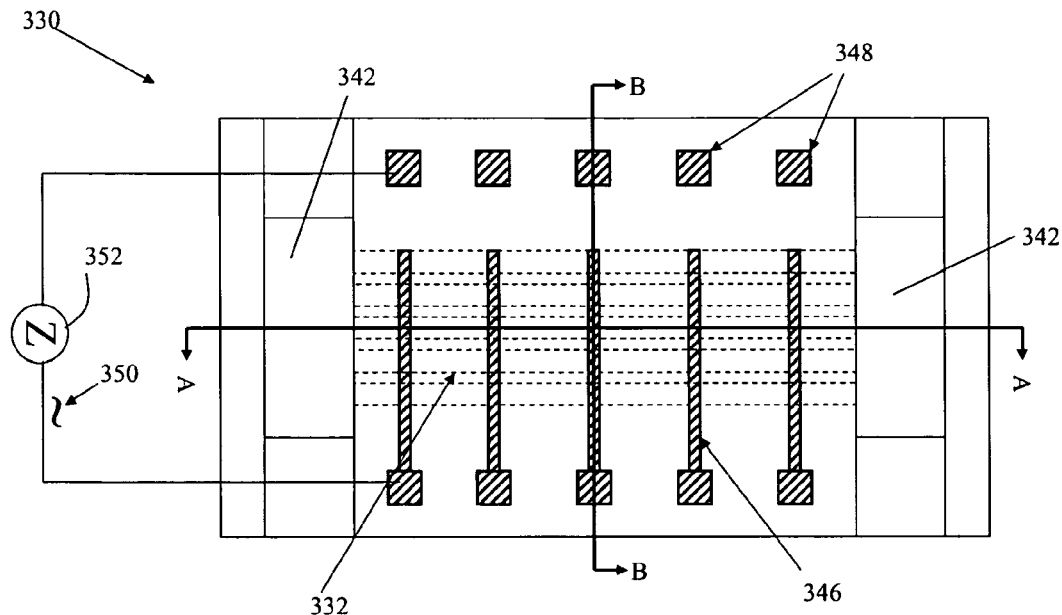

As shown in FIGS. 14a, 14b and 14c, an exemplary embodiment of a ECRS 330 for monitoring the process of cleaning, rinsing and drying of micro features in-situ comprises at least one and suitably several buried micro channels 332 in a dielectric layer 334 between dielectric (e.g., silicon dioxide ($SiO_2$), silicon nitride ($Si_3N_4$) and low-K organic materials) layers 336 and 338 and oriented substantially parallel to the dielectric stack and sensor's fluid-solid interface 340. The term "buried micro channel" is used to refer to a void micro structure formed below and parallel to the fluid-solid interface with at least one opening through a top dielectric layer to the fluid-solid interface.

At least one and suitably several pair of electrodes 346, 348 (e.g., Poly-Si, Aluminum or copper) in dielectric layers 336 and 338, respectively, at a fixed separation and spaced a known distance from the at least one opening are exposed to fluid in the micro-channel and configured to receive a measurement signal 350 and carry the measurement signal (voltage and current) to the micro channel. An impedance analyzer 352 measures the impedance of the micro channel between the electrodes (ratio of voltage and current and phase difference between the voltage and current). The micro sensor is suitably supported by a substrate 354 (e.g. a silicon wafer or a glass slide) having a covering dielectric layer 356. If the substrate is itself a dielectric the covering dielectric may be omitted. A capping dielectric layer 358 is formed over the micro sensor to avoid direct contact between the fluid and the electrode 346. Each micro channel has at least one opening and suitably two openings 342 through the dielectric layers 336, 358 between the channel 332 and the fluid-solid interface 340 for receiving fluid 344.

As shown, the micro sensor may be configured with multiple micro channels 332 to improve the reliability of the impedance measure. The micro channels are suitably identical but may have different geometries such as length (the maximum distance across the channel opening) and depth. If the micro channels have different depth, then complex mathematical deconvolution must be performed to determine the contribution of each channel length to the total impedance. Hence, unless the mathematical form of the dependence of impedance on depth is well-understood, it is not desirable to include micro channels of different depth in the same sensor. The micro channels have an aspect ratio greater than 1-to-1 (depth-to-width), typically greater than 3-to-1 and may exceed 100-to-1. Because the micro channels are formed in the plane of the dielectric there is really no limit on their depth, hence aspect ratio.

In order to get a more complete characterization of the residue in the micro channel, multiple electrode pairs 346, 348 can be used to measure the impedance of the micro channel(s) at different distances from the opening 342. The same electrode pair 346, 348 may be used to measure the impedance of multiple identical micro channels 332 to reduce the measurement noise by placing the micro channels in parallel.

Although not shown, the ECRS can be provided with a guard and buffer circuit similar to that described for the vertical void micro-feature to reduce the effects of parasitic capacitance on the measured impedance.

ECRS for Micro-Surfaces

The surface of the dielectric can be non-porous, in which case the surface cleaning process is rate limited by the desorption of species from the surface or by removal of the species away from the surface. The dielectric can also be porous, or have other micro features present in it. Furthermore, a cell (biologic or other) may be placed on the surface and monitored.

Figure 15:
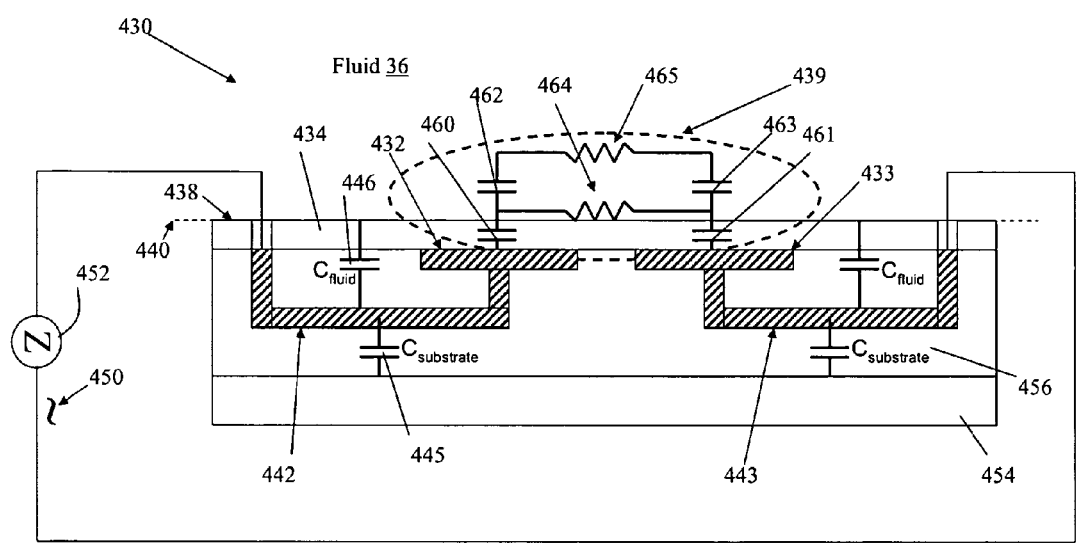
FIG. 15 is a section view of an embodiment of an ECRS for monitoring a micro-surface.

As shown in FIG. 15, an exemplary embodiment of a surface ECRS 430 for in-situ monitoring of the process of cleaning, rinsing and drying of surfaces and the micro features in those surfaces comprises two conducting electrodes 432 and 433 (e.g. copper or doped polysilicon with a typical thickness of 1 μm) that lie in the same plane, embedded in the surface of a supporting dielectric 456 on a substrate 454 (e.g. a silicon wafer or a glass slide), and covered by a thin dielectric layer 434 (e.g., silicon dioxide ($S_iO_2$), silicon nitride ($Si_3N_4$) and non-porous low-K organic dielectric materials). The covering dielectric may be as thin as a few nm, e.g. 10 nm or less, and the electrodes may be spaced as close a few microns, e.g. 2 μm or less. The "active" part of the electrodes lies on the surface of the supporting dielectric. A surface segment 439 of dielectric 434 is defined between the conducting electrodes at the fluid-solid interface 440. The electrodes are adapted to receive an ac measurement signal 450 to measure the impedance of surface segment 439 when the micro sensor is immersed in a fluid 436, being rinsed or drying. An impedance analyzer 452 measures the impedance (ratio of voltage and current and phase difference between the voltage and current) of the surface section 439 between the electrodes via connectors 442 and 443 (e.g. copper or doped polysilicon) embedded in the supporting dielectric 456 beneath the electrodes that carry the measurement signal 450 to electrodes 432 and 433.

Surface segment 439 has an electrical equivalent circuit consisting of capacitors 460 and 461 formed between the electrodes and the solution surface 438, capacitors 462 and 463 formed between electrodes and the surface double layers, the surface resistance 464 and the bulk fluid resistance 465. At solid-solution interfaces, an interface double layer forms because charges in the solution that are mobile (ions) respond to the presence of fixed charges on the solid. The interface double layer is responsible for capacitance $C_{dl}$ (capacitors 462 and 463) between the dielectric 434 and the solution 436, which forms an impedance $Z_{dl}=1/j\omega C_{dl}$ where ω is the measurement signal radial frequency in series with the bulk solution resistance and which shunts the surface resistance. The sensor can extract the individual components if the impedance measurement is performed over a range of measurement signal frequencies. Non-linear least squares fitting of the impedance data, a well known method from the domain of impedance spectroscopy, results in the individual component values.

Although not shown, the ECRS can be provided with a guard and buffer circuit similar to that described for the vertical void micro-feature to reduce the effects of parasitic capacitance on the measured impedance.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

1. A method for the manufacture of wafers, comprising:
   providing a production process for cleaning, rinsing and drying production wafers that include micro devices having micro features formed on or in a dielectric film, said production process providing a low resource solution in terms of solution and energy consumed subject to a constraint that each said cleaning, rinsing and drying process reach a specified impedance condition of the wafers' micro features within a specified time constraint, said reaching of the specified impedance condition based on in-situ impedance measurements of micro features in an electro-chemical residue sensor (ECRS) that are representative of the micro features on the production wafer, said ECRS used only during design of the production process; and
   processing production wafers through the cleaning, rinsing and drying processes controlled in accordance with the low resource solution of the production process, said production wafers processed without the ECRS.

2. The method of claim 1, wherein the production process specifies a chemical concentration and temperature for a cleaning solution based on the impedance measurements of the ECRS.

3. The method of claim 1, wherein the production process specifies a flow rate and temperature for a rinse solution based on the impedance measurements of the ECRS.

4. The method of claim 1, wherein the production process specifies a spin rate and temperature for a drying gas based on the impedance measurements of the ECRS.

5. The method of claim 1, further comprising:
   including another ECRS with the production wafers to monitor the impedance during production.

6. The method of claim 1, wherein at least one of the cleaning, rinsing and drying processes includes first and second sub-processes in which the rate of change of the measured impedance is substantially independent and dependent, respectively, of a process condition for at least one process variable, said low resource solution including different process conditions for said first and second sub-processes.

7. The method of claim 1, wherein the specified impedance condition comprises a value of an endpoint impedance.

8. The method of claim 1, wherein the specified impedance condition comprises a rate at which the impedance changes.

* * * * *